(12) United States Patent
Reid et al.

(10) Patent No.: US 6,544,933 B1
(45) Date of Patent: *Apr. 8, 2003

(54) DRILLING FLUID

(75) Inventors: Paul Ian Reid, St. Neots (GB); Bernadette Craster, Reach (GB); John Peter Crawshaw, Newmarket (GB); Terence George Balson, Feldmeilen (CH)

(73) Assignee: Schlumberger Technology Corporation, Sugar Land, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/011,938

(22) PCT Filed: Aug. 14, 1996

(86) PCT No.: PCT/GB96/01989

§ 371 (c)(1),
(2), (4) Date: Jul. 13, 1998

(87) PCT Pub. No.: WO97/07183

PCT Pub. Date: Feb. 27, 1997

(30) Foreign Application Priority Data

Aug. 17, 1995 (GB) ................................... 9516843

(51) Int. Cl.$^7$ ................................ C09K 7/02
(52) U.S. Cl. ........................ 507/136; 507/261
(58) Field of Search .............. 507/136, 139, 507/261

(56) References Cited

U.S. PATENT DOCUMENTS

| 2,996,551 | A | * | 8/1961 | De Groote | 507/136 |
| 3,079,337 | A | * | 2/1963 | Turbak et al. | 507/136 |
| 3,254,713 | A | * | 6/1966 | Scherr et al. | 507/136 |
| 4,719,021 | A | * | 1/1988 | Branch, III | 507/136 |
| 5,007,489 | A | * | 4/1991 | Enright et al. | 507/136 |

FOREIGN PATENT DOCUMENTS

| DE | 4302462 A1 | 6/1994 |
| EP | 0495579 A2 | 7/1992 |
| EP | 0702073 A1 | 3/1996 |
| GB | 2297774 A | 8/1996 |
| GB | 2297775 A | 8/1996 |
| WO | 94/14919 | 7/1994 |

* cited by examiner

Primary Examiner—Philip Tucker
(74) Attorney, Agent, or Firm—Bill Wang; Thomas O. Mitchell; Catherine Menes

(57) ABSTRACT

A water-based drilling fluid (WBM) comprises as additive a reaction product of a polyhydroxyalkane and alkylene oxide. The polyhydroxyalkane is desirably based on a monosaccharide, and is preferably sorbitol. The alkylene oxide may comprise ethylene oxide (EO), propylene oxide (PO) and/or butylene oxide (BO). Good results have been obtained with additives including Sorbitol+18EO, Sorbitol+9PO, Sorbitol+4EO+6BO, Sorbitol+6EO+6BO, or Sorbitol+6BO. Drilling fluids in accordance with the invention have been found in laboratory tests to exhibit improved shale inhibition properties as compared with known polyol containing WBM, particularly in the absence of added potassium ions. This is environmentally advantageous.

57 Claims, No Drawings

DRILLING FLUID

This invention concerns drilling fluids, particularly water-based drilling fluids.

BACKGROUND OF THE INVENTION

Drilling fluids are used in well drilling operations, eg during drilling of oil and gas wells. During drilling, drilling fluid is pumped down a drillstring, discharged through ports in the drill bit and returned to the surface via the annulus between the drillpipe and the surrounding formation. The drilling fluid performs a variety of functions including cooling and lubricating the drill bit and drillstring, removing rock cuttings generated during the drilling process and carrying them to the surface, suspending cuttings in the annulus when pumping stops, preventing squeezing in or caving of the formation and keeping formation fluids at bay.

Drilling fluids generally comprise a carrier, a weighting agent and chemical additives. Drilling fluids fall into two main categories: water-based drilling fluids, also known as water based muds (WBM), in which the carrier is an aqueous medium; and oil-based drilling fluids, also known as oil-based muds (OBM), in which the carrier is oil. OBM are technically superior to WBM in certain important respects, including the comparative lack of adverse reactivity of OBM with shales, one of the most commonly encountered rock types during drilling for oil and gas. Use of OBM, however, has the disadvantage of resulting in production of large quantities of oil-contaminated waste products such as cuttings that are difficult to dispose of in an environmentally acceptable way. While use of WBM is environmentally more acceptable than OBM, the performance of WBM, particularly when drilling through water sensitive rocks such as shales, is technically inferior to that of OBM. Shales exhibit great affinity for water, and adsorption of water by shales causes the shale to swell and produces chemical changes in the rock which produce stresses that weaken the formation, possibly leading to erosion of the borehole or loss of structure. This can lead to drilling problems such as stuck pipe. In addition inferior wellbore quality may hinder logging and completion operations.

Much effort has been put into improving the performance of WBM relative to shales, namely improving the level of so called shale inhibition of WBM. Various chemical additives have been incorporated in WBM in attempts to improve shale inhibition. In particular water soluble glycols or polyols (ie. molecules containing more than one hydroxyl groups) are widely used for this purpose, typically being added to WBM in amounts in the range 3 to 10% by weight. Polyols used in this way include, for example, glycerols, polyglycerols, glycols, polyalkylene glycols (PAG), eg polyethylene glycols (PEG), polypropylene glycols (PPG) and copolymers of ethylene and propylene glycols, alcohol ethoxylates (AET) and glycol ethers. A typical inhibitive AET is an n-butanol derivative of ethylene oxide. The PAGs can have a range of ethylene oxide: propylene oxide (EO:PO) ratios and can be random or block copolymers; a frequently used material of this type is understood to be a random copolymer with an EO:PO ratio of about 1:1. See, for example EP 0495579, U.S. Pat. No. 4,830,765, U.S. Pat. No. 4,172,800. For further discussion of this subject see, for instance, The Society of Petroleum Engineers Reports SPE 25989 (Reduced Environment Impact and Improved Drilling Performance With Water-Based Muds Containing Glycols) and SPE 28818 (Water Based Glycol Drilling Muds—Shale Inhibition Mechanisms) and also Schlumberger Oilfield Review, April 1994, pages 33 to 43 (Designing and Managing Drilling Fluid).

SPE 28960 (Mechanism of Shale Inhibition by Polyols in Water Based Drilling Fluids) proposes a credible mechanism that adequately describes how such polyols provide shale inhibition. In summary, this publication teaches that two processes are important:

The polyols interact with potassium ions on the surfaces of the fine-grained clay minerals that are present in reactive shales. These potassium ions are hydrated but their low hydration energy means that water is easily removed from the cation and the polyol forms a stable complex. Water is less easily removed from sodium or calcium ions and the resulting cation/polyol complexes are weaker: the authors believe this explains the higher level of inhibition obtained with polyols in the presence of potassium. All the established inhibitive polyols studied by the authors are said to derive the bulk of their activity by this mechanism. Other weakly hydrated cations (eg ammonium or caesium) behave in the same way as potassium.

A second, but minor, contribution to inhibition is observed with currently available EO:PO polymers. Here, the authors provide evidence of interactions between adjacent polyol molecules adsorbed on the clay surfaces. These interactions are independent of the concentration and composition of the aqueous salt solution and, since they are absent in the PEG and n-butanol ethoxylate molecules, they assume them to be due to the intermolecular interactions between mildly hydrophobic methyl groups in the PO portions of the EO:PO copolymers. This interaction is sufficient to make EO:PO polymers mildly inhibitive to shales in distilled water, where molecules such as PEG and AET rarely show any degree of inhibition.

The shale inhibition properties of polyol-containing WBM can be enhanced by incorporation of potassium salts, eg potassium chloride, possibly in combination with gypsum. However, the shale inhibition properties of even the best known potassium and polyol-containing WBM are much inferior to those of OBM. Further, the use of potassium can present waste disposal problems, as there are certain regions, eg. The Gulf of Mexico, where the discharge of potassium to the environment is prohibited or severely restricted. In addition, the use of potassium-containing WBM can present problems in land drilling where the contamination of ground water by potassium-containing drilling waste is.considered unacceptable.

It has now been found that the shale inhibition properties of WBM can be improved by use of novel polyol additives in the form of reaction products of polyhydroxyalkanes (also known as alditols) and alkylene oxides.

SUMMARY OF THE INVENTION

According to the present invention there is provided a water-based drilling fluid comprising as additive a reaction product of a polyhydroxyalkane and alkylene oxide.

The polyhydroxyalkane may be linear or branched and may include -up to 20 carbon atoms. The polyhydroxyalkane is preferably based on a monosaccharide, conveniently being a molecule such as glycerol, erythritol, threitol, ribitol, sorbitol, mannitol and galactitol. The currently preferred polyhydroxyalkane is sorbitol.

The alkylene oxide conveniently comprise ethylene oxide (EO), propylene oxide (PO) and/or butylene oxide (BO). Mixtures of alkylene oxides may be used.

Reaction products of polyhydroxyalkanes and alkylene oxides may be readily produced by polymerisation reactions, such as base catalysed polymerisations. Such products are obtainable commercially from a number of sources, including Dow Chemical, ICI and Hoechst.

The additive comprises a polyhydroxyalkane with at least one alkylene oxide chemically linked at one or both ends thereof, preferably at both ends forming generally symmetrical molecules. The number and nature of the alkylene oxide units is not critical provided the molecule is not too viscous, is at least partially soluble in aqueous fluids and has suitable foaming characteristics. Viscosity, insolubility and foaming tend to increase with increasing molecular weight, so larger numbers of EO units can be tolerated than is the case for PO and BO units. The additive conveniently comprises up to 30 EO units (generally 15 linked linearly to each end of the polyhydroxyalkane), or smaller numbers of PO units, BO units, of mixtures of EO, PO and/or BO in any ratio.

Good results have been obtained with additives including Sorbitol+18EO, Sorbitol+9PO, Sorbitol+4EO+6BO, Sorbitol+6EO+6BO, or Sorbitol+6BO.

A mixture of different additives in accordance with the invention may be used.

The additives are typically used in WBM in amounts in the range 1 to 10% by weight, preferably 1 to 5% by weight.

The drilling fluid of the invention may otherwise be of conventional formulation, with the aqueous medium typically comprising fresh water, salt water, other salt solutions or mixtures thereof.

Other additives may be included in the drilling fluid in conventional manner. In particular, potassium ions, eg from potassium chloride, may be included to improve shale inhibition properties.

Drilling fluids in accordance with the invention have been found in laboratory tests to exhibit improved shale inhibition properties as compared with known polyol-containing WBM, particularly in the absence of added potassium ions. This is environmentally advantageous, as discussed above.

The mechanisms of shale inhibition is not at present fully understood, but it is thought (without wishing to be bound by theory) that the improved shale inhibition properties obtained with the drilling fluids of the invention may result from enhanced hydrophobic interaction between adjacent polyol additive molecules adsorbed on clay surfaces of shales due to the increased hydrophobicity of the polyol resulting from the presence of the polyhydroxyalkane. An alternative explanation, which is also credible, is that these molecules are effective at disrupting the organisation of water molecules near the surfaces of clay minerals. This organisation has been proposed as a mechanism for the swelling of clay minerals in aqueous fluids.

The invention will be further described, by way of illustration, in the following Example.

EXAMPLE

The level of shale inhibition provided by different drilling fluid additives and formulations is routinely assessed by a number of laboratory techniques. Tests such as cuttings dispersion and shale swelling are suitable for the rapid screening of new additives and are widely use in the industry. A good indication of the inhibitive properties of an additive can also be obtained by a modification of the standard oilfield cuttings dispersion test. This approach is particularly suitable for screening low viscosity, water-soluble species such as polyols and fully formulated drilling fluids containing the additives.

In this test, a known weight of shale cuttings (approximately 20 g) is added to a measured volume of test fluid (approximately 350 ml) in a container. The container is rotated such that the cuttings are in a constant state of agitation in the fluid; this encourages breakdown and dispersion of the cuttings if they become softened due to interaction with the test fluid. At the end of the test period, the cuttings that remain undispersed are collected, washed, dried and weighed. The recovered weight is expressed as a percentage of the original weight added to the test fluid. Clearly, the more inhibitive the test fluid, the lower the level of cuttings dispersion and hence the higher the final recovery figure.

The results of these tests are given in Tables 1 and 2 for two different types of shale. Two polyols used for comparison were polyethylene glycol (PEG) and polyalkylene glycol (PAG); both of these are currently used as shale inhibitors in commercial systems. The average molecular weights of these materials were about 600 and 650 respectively. The PAG was a random copolymer of EO and PO with an EO:PO ratio of approximately 1:1. The polyols of this invention all comprised sorbitol and combinations of EO, PO and BO as described in Tables 1 and 2.

TABLE 1

Recovery of Oxford Clay Cuttings From Test Fluid Comprising; de-ionised water, 10 g/liter low viscosity carboxymethyl cellulose, 4 g/liter Xanthan gum.

Test polyols were used at concentrations as stated.

| Polyol | Concentration in Test Fluid (%) | Approximate Polyol Composition | Cuttings Recovery (%) |
|---|---|---|---|
| Base fluid | | | |
| no polyol | 0 | | 24 |
| PEG | 6.5 | Polyethylene glycol | 24 |
| PAG | 5 | Mixed polyethylene/ polypropylene glycol | 26 |
| M1 | 1 | Sorbitol + 18EO | 34 |
| M1 | 5 | Sorbitol + 18EO | 36 |
| M2 | 1 | Sorbitol + 9PO | 37 |
| M3 | 1 | Sorbitol + 4EO + 6BO | 33 |
| M4 | 1 | Sorbitol + 6EO + 6BO | 40 |
| M5 | 1 | Sorbitol + 6BO | 43 |

TABLE 2

Recovery of London Clay Cuttings From Test Fluids Comprising De-ionised Water, Synthetic Seawater or De-ionised Water + 7 wt % KCl. All polyol concentrations 5% except PEG (6.5%).

| Polyol | Base Fluid | Approximate Polyol Composition | Cuttings Recovery (%) |
|---|---|---|---|
| None | De-ionised water | | 9 |
| PEG | De-ionised water | polyethylene glycol | 5 |
| PAG | De-ionised water | Mixed polyethylene/ polypropylene glycol | 51 |
| M2 | De-ionised water | Sorbitol + 9PO | 90 |
| None | Synthetic seawater | | 50 |
| PEG | Synthetic seawater | Polyethylene glycol | 24 |
| PAG | Synthetic seawater | Mixed polyethylene/ polypropylene glycol | 91 |
| M2 | Synthetic seawater | Sorbitol + 9PO | 93 |
| None | De-ionised water + KCl | | 72 |
| PEG | De-ionised water + KCl | Polyethylene glycol | 90 |

TABLE 2-continued

Recovery of London Clay Cuttings From Test Fluids Comprising De-ionised Water, Synthetic Seawater or De-ionised Water + 7 wt % KCl. All polyol concentrations 5% except PEG (6.5%).

| Polyol | Base Fluid | Approximate Polyol Composition | Cuttings Recovery (%) |
|---|---|---|---|
| PAG | De-ionised water + KCl | Mixed polyethylene/ polypropylene glycol | 92 |
| M2 | De-ionised water + KCl | Sorbitol + 9PO | 94 |

The results clearly show the improved levels of inhibition provided by fluids which do not contain potassium chloride when the sorbitol-based polyols are used in place of polyols in current commercial use.

Similar experiments have been carried out with additives based on other polyhydroxyalkanes including mannitol and glycerol. The results were inferior when glycerol was substituted for sorbitol in the above molecules.

What is claimed is:

1. A water-based shale stabilizing drilling fluid comprising as additive a reaction product of a polyhydroxyalkane and an alkylene oxide wherein the additive is at least partially soluble in aqueous fluids, comprises molecules each having a total polyhydroxyalkane content of up to 20 carbon atoms and up to 30 alkylene oxide units and is other than a polyalkylene glycol.

2. The drilling fluid of claim 1 in which the polyhydroxyalkane comprises glycerol, erythritol, threitol, ribitol, sorbitol, mannitol, or galactitol.

3. The drilling fluid of claim 1 in which the alkylene oxide comprises ethylene oxide (EO), propylene oxide (PO) or butylene oxide (BO) or mixtures thereof.

4. The drilling fluid of claim 1 in which the additive is selected from a group comprising Sorbitol+18EO, Sorbitol+9PO, Sorbitol+4EO+6BO, Sorbitol+6EO+6BO, Sorbitol+6BO.

5. The drilling fluid of claim 1 in which the additive is present in an amount in the range of 1 to 5% by weight.

6. The drilling fluid of claim 1 comprising an aqueous medium of fresh or salt water.

7. A water-based shale stabilizing drilling fluid comprising:
as additive a reaction product, other than a polyalkylene glycol, at least partially soluble in aqueous fluids, of a polyhydroxyalkane and an alkylene oxide; and
a potassium salt.

8. The drilling fluid of claim 7 in which the potassium salt comprises potassium chloride.

9. A method of drilling a wellbore using a water-based drilling fluid, the method comprising the steps of:
drilling a wellbore through an underground formation including shale; and
pumping a water-based drilling fluid down into the wellbore while drilling, the drilling fluid comprising as additive a reaction product, other than a polyalkylene glycol, at least partially soluble in aqueous fluids, of a polyhydroxyalkane and an alkylene oxide, thereby stabilizing the shale.

10. A method according to claim 9 wherein the additive comprises molecules each having a total polyhydroxyalkane content of up to 20 carbon atoms and up to 30 alkylene oxide units.

11. A method according to claim 9 wherein the alkylene oxide comprises ethylene oxide (EO), propylene oxide (PO) and/or buylene oxide (BO).

12. A method according to claim 9 wherein the additive is selected from a group comprising Sorbitol+18EO, Sorbitol+9PO, Sorbitol+4EO+6BO, Sorbitol+6EO+6BO, Sorbitol+6BO.

13. A method according to claim 9 wherein the additive is present in an amount in the range 1 to 10% by weight.

14. A method according to claim 13 wherein the additive is present in an amount in the range 1 to 5% by weight.

15. A method according to claim 9 wherein the drilling fluid comprises an aqueous medium of fresh water or salt water.

16. A method according to claim 9 wherein the drilling fluid further comprises a potassium salt additive.

17. A method according to claim 16 wherein the potassium salt comprises potassium chloride.

18. The drilling fluid of claim 1 in which the polyhydroxyalkane is sorbitol.

19. The drilling fluid of claim 1 in which the additive comprises an alkylene oxide chemically linked at both ends of the polyhydroxyalkane thereof.

20. The drilling fluid of claim 1 in which the additive forms a symmetrical molecule.

21. A water-based shale stabilizing drilling fluid comprising as additive a reaction product of a polyhydroxyalkane selected from the group consisting of erythritol, threitol, ribitol, sorbitol, mannitol and galactitol and an alkylene oxide wherein the additive comprises molecules each having a total polyhydroxyalkane content of up to 20 carbon atoms and up to 30 alkylene oxide units.

22. The drilling fluid of claim 21 in which the additive comprises an alkylene oxide chemically linked at both ends of the polyhydroxyalkane thereof.

23. The drilling fluid of claim 21 in which the additive forms a symmetrical molecule.

24. The drilling fluid of claim 21 in which the alkylene oxide comprises ethylene oxide (EO), propylene oxide (PO,) butylene oxide (BO), or mixtures thereof.

25. The drilling fluid of claim 21 in which the polyhydroxyalkane is sorbitol.

26. The drilling fluid of claim 21 in which the additive is selected from the group consisting of sorbitol+18EO, sorbitol+9PO, sorbitol+4EO+6BO, sorbitol+6EO+6BO, and sorbitol+6BO.

27. The drilling fluid of claim 21 in which the additive is present in an amount in the range of 1% to 10% by weight.

28. The drilling fluid of claim 21 in which the additive is present in an amount in the range of 1 to 5% by weight.

29. The drilling fluid of claim 21 comprising an aqueous medium of fresh water or salt water.

30. A water-based shale stabilizing drilling fluid comprising:
as additive a reaction product of a polyhydroxyalkane selected from the group consisting of erythritol, threitol, ribitol, sorbitol, mannitol and galactitol, and an alkylene oxide; and
a potassium salt.

31. The drilling fluid of claim 30 in which the potassium salt comprises potassium chloride.

32. A method of drilling a wellbore using a water-based drilling fluid, the method comprising the steps of:
drilling a wellbore through an underground formation including shale; and
pumping a water-based drilling fluid down into the wellbore while drilling, the drilling fluid comprising as additive a reaction product of a polyhydroxyalkane selected from the group consisting of erythritol, threitol, ribitol, sorbitol, mannitol and galactitol, and an alkylene oxide, thereby stabilizing the shale.

33. The method of claim 32 wherein the additive comprises molecules each having a total polyhydroxyalkane carbon content of up to 20 carbon atoms and up to 30 alkylene oxide units.

34. The method of claim 32 wherein the alkylene oxide is selected from the group consisting of ethylene oxide (EO), propylene oxide (PO), butylene oxide (BO), and mixtures thereof.

35. The method of claim 32 wherein the additive is selected from the group consisting of sorbitol+18EO, sorbitol+9PO, sorbitol+4EO+6BO, sorbitol+6EO+6BO, and sorbitol+6BO.

36. The method of claim 32 wherein the additive is present in an amount in the range 1 to 10% by weight.

37. The method of claim 36 wherein the additive is present in an amount in the range 1 to 5% by weight.

38. The method according to claim 32 wherein the drilling fluid comprises an aqueous medium of fresh water or salt water.

39. The method according to claim 32 wherein the drilling fluid further comprises a potassium salt additive.

40. The method of claim 39 wherein the potassium salt comprises potassium chloride.

41. A water-based shale stabilizing drilling fluid comprising as additive a reaction product of a polyhydroxyalkane selected from the group consisting of erythritol, threitol, ribitol, sorbitol, mannitol and galactitol and deriving from a monosaccharide and an alkylene oxide wherein the additive is at least partially soluble in aqueous fluids and comprises molecules each having a total polyhydroxyalkane content of up to 20 carbon atoms and up to 30 alkylene oxide units.

42. The drilling fluid of claim 41 in which the additive comprises an alkylene oxide chemically linked at both ends of the polyhydroxyalkane thereof.

43. The drilling fluid of claim 41 in which the additive forms a symmetrical molecule.

44. The drilling fluid of claim 41 in which the alkylene oxide is selected from the group consisting of ethylene oxide (EO), propylene oxide (PO), butylene oxide (BO), and mixtures thereof.

45. The drilling fluid of claim 41 in which the polyhydroxyalkane is sorbitol.

46. The drilling fluid of claim 41 in which the additive is selected from the group consisting of sorbitol+18EO, sorbitol+9PO, sorbitol+4EO+6BO, sorbitol+6EO+6BO, and sorbitol+6BO.

47. The drilling fluid of claim 41 in which the additive is present in an amount in the range of 1% to 10% by weight.

48. The drilling fluid of claim 41 in which the additive is present in an amount in the range of 1 to 5% by weight.

49. The drilling fluid of claim 41 comprising aqueous medium of fresh water, salt water, other salt solutions or mixtures thereof.

50. The drilling fluid of claim 41 comprising a potassium salt.

51. The drilling fluid of claim 50 in which the potassium salt comprises potassium chloride.

52. A method of drilling a wellbore using a water-based drilling fluid, the method comprising the steps of:
    drilling a wellbore through an underground formation including shale; and
    pumping a water-based drilling fluid down into the wellbore while drilling, the drilling fluid comprising as additive a reaction product, at least partially soluble in aqueous fluids, of a polyhydroxyalkane deriving from a monosaccharide, and an alkylene oxide, thereby stabilizing the shale, wherein the additive is selected from the group consisting of sorbitol+18EO, sorbitol+9PO, sorbitol+4EO+6BO, sorbitol+6EO+6BO and sorbitol+6BO.

53. The method of claim 52 wherein the additive is present in an amount in the range 1 to 10% by weight.

54. The method of claim 53 wherein the additive is present in an amount in the range 1 to 5% by weight.

55. The method according to claim 52 wherein the drilling fluid comprises an aqueous medium of fresh water or salt water.

56. The method according to claim 52 wherein the drilling fluid further comprises a potassium salt additive.

57. The method of claim 56 wherein the potassium salt comprises potassium chloride.

* * * * *